United States Patent [19]
Tuy

[11] Patent Number: 6,097,784
[45] Date of Patent: Aug. 1, 2000

[54] 3D IMAGE RECONSTRUCTION FOR HELICAL PARTIAL CONE BEAM DATA

[75] Inventor: Heang K. Tuy, Chesterland, Ohio

[73] Assignee: Picker International, Inc., Highland Heights, Ohio

[21] Appl. No.: 09/164,013

[22] Filed: Sep. 30, 1998

[51] Int. Cl.$^7$ .................................................... A61B 6/03
[52] U.S. Cl. ................................. 378/4; 378/15; 378/901
[58] Field of Search ............................. 378/4, 8, 15, 19, 378/901

[56] References Cited

U.S. PATENT DOCUMENTS

| | | | |
|---|---|---|---|
| 4,789,929 | 12/1988 | Nishimura et al. | 378/15 |
| 5,073,911 | 12/1991 | Ozaki et al. | 378/17 |
| 5,090,037 | 2/1992 | Toth et al. | 378/4 |
| 5,377,250 | 12/1994 | Hu | 378/15 |
| 5,404,293 | 4/1995 | Weng et al. | 378/15 |
| 5,485,493 | 1/1996 | Heuscher et al. | 378/15 |
| 5,625,660 | 4/1997 | Tuy | 378/15 |

OTHER PUBLICATIONS

"Technique and Arrangement for Tomographic Imaging," PCT Application of Danielsson, et al. (Jan. 13, 1998).

Defrise, et al., "A Cone–Beam Reconstruction Algorithm Using Shift–Variant Filtering and Cone–Beam Backprojection," *IEEE Transactions on Medical Imaging*, (Mar. 1994) vol. 13, No. 1, pp. 186–195.

*Primary Examiner*—David V. Bruce
*Attorney, Agent, or Firm*—Fay, Sharpe, Fagan, Minnich & McKee, LLP

[57] ABSTRACT

A method of image reconstruction from partial cone beam data includes collecting the partial cone beam data in two-dimensional arrays. The collected data corresponds to rays of radiation diverging in two dimensions from a common vertex as the vertex travels along a curve. Each element of the data represents a line integral of an object being reconstructed taken along each ray. The data is then pre-weighted and a local coordinate system is defined. A one-dimensional convolution of the pre-weighted data is computed in the local coordinate system along a direction which is tangential to the curve along which the vertex travels. Finally, the convolved data is weighted and three-dimensionally backprojected. In a preferred embodiment, the curve defines a helical path, and the kernel for the one-dimensional convolution of the pre-weighted data is a ramp convolver.

18 Claims, 6 Drawing Sheets

3D IMAGE RECONSTRUCTION FOR HELICAL PARTIAL CONE BEAM DATA

BACKGROUND OF THE INVENTION

The present invention relates to the art of image reconstruction. It finds particular application in conjunction with CT scanner, and will be described with particular reference thereto. However, it is to be appreciated that the present invention is also amenable to other like applications.

Conventionally, spiral CT scanners include an x-ray source which projects a thin slice or beam of radiation. The x-ray source is mounted for rotational movement about a subject who is moving along the axis of rotation. An arc or ring of radiation detectors receive radiation which has traversed the subject. Data from the radiation detectors represents a single spiraling slice through the subject. The data from the detectors is reconstructed into a three-dimensional image representation.

For faster data collection, a pair or more of radiation detectors can be disposed next to each other. This enables two or more slices of data to be collected concurrently. However, like the single slice scanner, only intra-slice data is used in the reconstruction process.

One of the difficulties with such prior art scanners is that they place major stress on the x-ray generator. When a solid geometric shape of x-rays, such as a cone, are generated, the x-rays pass through a volumetric region of the subject. In true cone beam reconstruction, truncation of the data is not permitted. These x-rays pass along known rays, both within traditional planes and at acute angles through several planes. The radiation passing through rays at an angle to the central plane were previously lost to collimation. By utilizing the radiation previously lost in collimation to generate useful diagnostic information, the load on the x-ray generator is reduced.

However, images reconstructed from data collected along divergent beams tend to have artifacts. One way of minimizing the divergent ray artifacts is to minimize the number of rings, i.e., limit the width of the cone beam. Of course, limiting the width of the cone beam partially defeats the original intent.

Although the additional radiation supplied by the cone beam is beneficial in imaging, it has the detrimental side effect of increasing the dosage to the subject. On the other hand, the high dosage enables a volume to be reconstructed with fewer rotations of the cone beam.

In U.S. Pat. No. 5,625,660, commonly assigned and incorporated herein by reference, an image reconstruction technique for helical partial cone-beam data is disclosed.

However, that technique divides the data stream into two parts which are processed separately and then recombined. In general, this is less efficient and more complicated than processing a single data stream.

The present invention contemplates a new and improved image reconstruction technique which overcomes the above-referenced problems and others.

SUMMARY OF THE INVENTION

In accordance with one aspect of the present invention, a method of image reconstruction from partial cone beam data is provided. The method includes collecting the partial cone beam data in two-dimensional arrays. The collected data corresponds to rays of radiation diverging in two dimensions from a common vertex as the vertex travels along a curve. Each element of the data is related to line integrals of an object being reconstructed taken along each ray. A local coordinate system is defined and the data is pre-weighted. A one-dimensional convolution of the pre-weighted data is computed in the local coordinate system along a direction which is tangential to the curve along which the vertex travels. The convolved data is then weighted and three-dimensionally backprojected.

In accordance with a more limited aspect of the present invention, for each position of the vertex as it travels along the curve, the data collected is not truncated in a direction parallel to the tangent of the curve at the position of the vertex and is truncated in at least one other orthogonal direction.

In accordance with a more limited aspect of the present invention, the curve along which the vertex travels is a differentiable curve in three-dimensional space arranged such that any plane going through a point of reconstruction intersects the curve at least once.

In accordance with a more limited aspect of the present invention, the curve defines a helical path.

In accordance with a more limited aspect of the present invention, the kernel for the one-dimensional convolution of the pre-weighted data is a ramp convolver.

In accordance with a more limited aspect of the present invention, the weighting of the convolved data is proportional to a summation of values of a multiplicity function. The values correspond to all planes going through the vertex and the point of reconstruction.

In accordance with a more limited aspect of the present invention, values of the multiplicity function are determined based on a number of intersections corresponding planes going through the vertex and the point of reconstruction have with a portion of the helical path traveled by the vertex to collect enough data for one complete reconstruction.

In accordance with a more limited aspect of the present invention, the multiplicity function includes terms corresponding to each intersection. The terms have values based on the intersections' relative level to the point of reconstruction.

In accordance with a more limited aspect of the present invention, when the intersections are at a level equal to that of the point of reconstruction, their corresponding terms are fully valued, and as intersections gradually go to a level one-half revolution away from that of the point of reconstruction, their corresponding term values gradually go to zero.

In accordance with a more limited aspect of the present invention, the weighting of the convolved data is inversely proportional to the square of the distance between the vertex and the point of reconstruction.

In accordance with another aspect of the present invention, a CT scanner includes a first gantry which defines an examination region. A rotating gantry is mounted on the first gantry for rotation about the examination region. A source of penetrating radiation is arranged on the rotating gantry for rotation therewith. The source of penetrating radiation emits a cone-shaped beam-of radiation that passes through the examination region as the rotating gantry rotates. A subject support holds a subject being examined at least partially within the examination region and at least one of the first gantry and the subject support is translated such that the subject passes through the examination region while the rotating gantry is rotated. In this manner, the source of penetrating radiation follows a helical path relative to the subject. A two-dimensional array of radiation detectors is arranged to receive the radiation emitted from the source of penetrating radiation after it has traversed the examination region. A reconstruction processor reconstructs images of the subject from data collected by the two-dimensional array of radiation detectors. The reconstruction processor includes a first data processor which pre-weights the data. A convolver takes the data from the first data processor and performs a one-dimensional convolution on it in a local coordinate system along a direction which is tangential to the helical path. A second data processor takes the data from the convolver and weights it. A backprojector then takes the data from the second data processor and three-dimensionally backprojects it into an image memory. A human viewable display accesses the image memory to display reconstructed images of the subject.

One advantage of the present invention is increased efficiency in the reconstruction process.

Another advantage of the present invention is the simplification of the reconstruction process for partial cone beam data.

Yet another advantage of the present invention is the achievement of high-quality images reconstructed from partial data sets, i.e., the data may be truncated in at least one direction without a loss of image quality.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
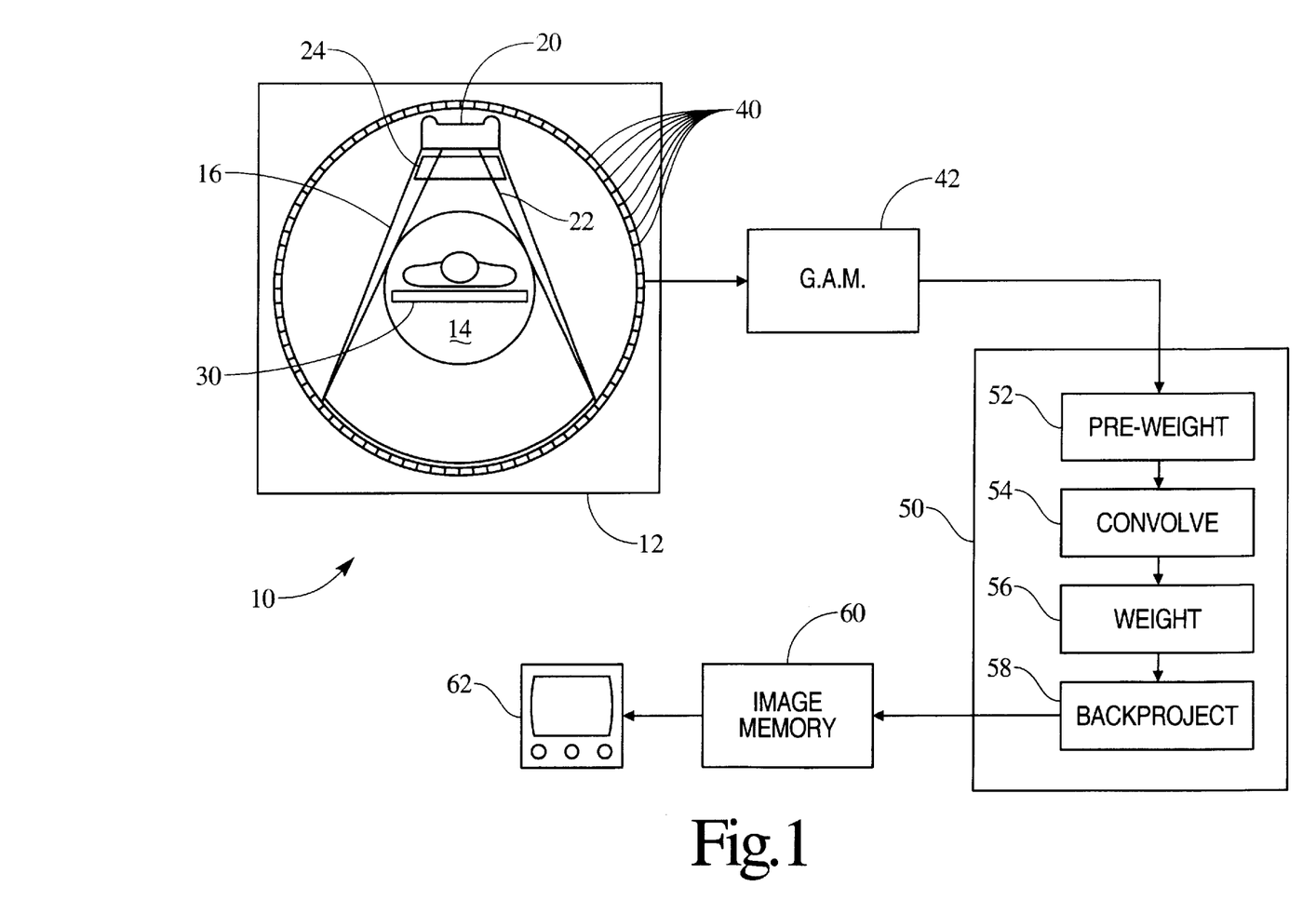
FIG. 1 is a diagrammatic illustration of a CT scanner in accordance with aspects of the present invention; and, FIGS. 2 through 6 are drawings used to illustrate the derivation and implementation of the reconstruction process in accordance with aspects of the present invention.

With reference to FIG. 1, a CT scanner 10 includes a stationary gantry 12 which defines an examination region 14. A rotating gantry 16 is mounted on the stationary gantry 12 for rotation about the examination region 14. A source of penetrating radiation 20, such as an x-ray tube, is arranged on the rotating gantry 16 for rotation therewith. The source of penetrating radiation produces a cone-shaped beam of radiation 22 that passes through the examination region 14 as the rotating gantry 16 rotates. A collimator and shutter assembly 24 forms the beam of radiation 22 and selectively gates the beam 22 on and off. Alternately, the radiation beam 22 is gated on and off electronically at the source 20.

A subject support 30, such as a couch or the like, suspends or otherwise holds a subject being examined or imaged at least partially within the examination region 14. Moreover, as the rotating gantry 16 rotates, the support 30, and consequently the subject thereon, are translated along a central horizontal axis of the examination region 14. In this manner, the source 20 follows a helical path relative to the subject. Optionally, in an alternative embodiment, the support 30 remains stationary while the "stationary gantry" 12 is translated or otherwise moved relative to the subject such that the source 20 follows a helical path relative thereto.

In the illustrated fourth generation CT scanner, a plurality of rings of radiation detectors 40 are mounted peripherally around the examination region 14 on the stationary gantry 12. Alternately, in a preferred embodiment, a third generation CT scanner is employed with the radiation detectors 40 mounted on the rotating gantry 16 on a side of the examination region 14 opposite the source 20 such that they span the area defined by the cone-shaped beam of radiation 22. Regardless of the configuration, the radiation detectors 40 are arranged such that a two-dimensional array thereof receive the radiation emitted from the source 20 after it has traversed the examination region 14.

Figure 6:
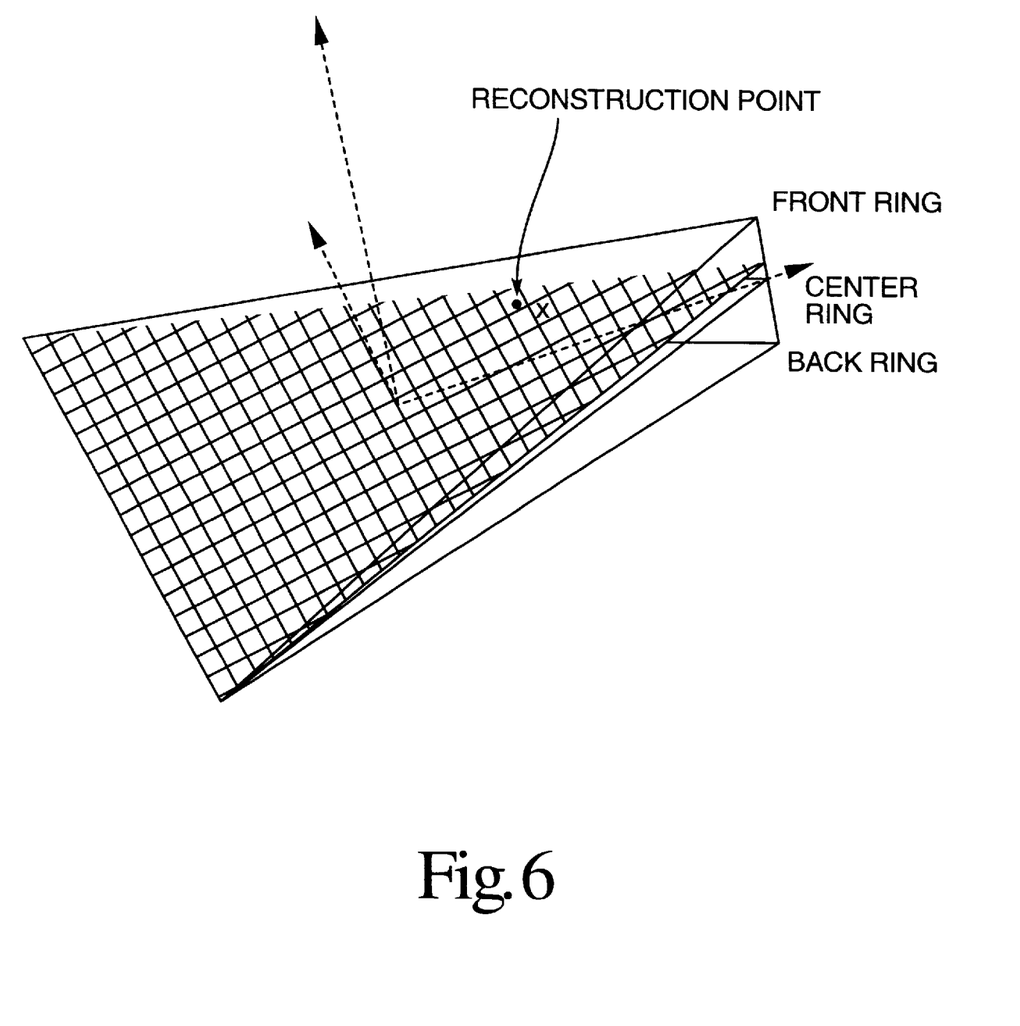

In a source cone geometry, an array of detectors which span the radiation 22 emanating from the source 20 are sampled concurrently at short time intervals as the source 20 rotates behind the examination region 14 to generate a source view. In a detector geometry (as seen in FIG. 6), the detectors are sampled a multiplicity of times as the source 20 rotates behind the examination region 14 to generate a detector view. The path between the source 20 and each of the radiation detectors 40 is denoted as a ray.

The radiation detectors 40 convert the detected radiation into electronic data. That is to say, each of the radiation detectors produces an output signal which is proportional to the intensity of received radiation. Optionally, a reference detector may detect radiation which has not traversed the examination region 14. A difference between the magnitude of radiation received by the reference detector and each active radiation detector 40 provides an indication of the amount of radiation attenuation along a corresponding ray of sampled radiation.

In detector view geometry, each view or two-dimensional array of data represents a cone of rays having its vertex at one of the radiation detectors 40 collected over a short period of time as the source 20 rotates behind the examination region 14 from the detectors. In source view geometry, each view or two-dimensional array of data represents a cone of rays having a vertex at the source 20 collected by a concurrent sampling of detectors.

A gantry acquisition memory board 42 receives sampled data from the radiation detectors 40. The gantry acquisition memory board 42 optionally shuffles the data to transform it from a detector cone geometry to a source cone geometry or vice versa and performs a ripple filtering operation before passing the data to an image processor 50. The image processor 50 processes the view data from the gantry acquisition board 42 and three-dimensionally backprojects it into an image memory 60.

The image processor 50 performs mathematical manipulations which convolve each view with an appropriate filter or convolution function for the view format. More specifically, a first data processor 52 pre-weights the data. A convolver 54 then performs a one-dimensional convolution. After a second data processor 56 weights the convolved data, a backprojector 58 three-dimensionally backprojects the data into the image memory 60. A human viewable display 62, such as a monitor, accesses the image memory to selectively display reconstructed images of the scanned subject.

With reference to FIGS. 2–6 and continuing reference to FIG. 1, as a mathematical foundation for the reconstruction procedure, an "exact inversion formula" is established. Unlike the classical inversion formula for reconstruction of a two-dimensional (2D) subject from a set of fan beam data, the inversion formula herein assumes that: (i) the subject is represented by a true three-dimensional (3D) real function, (ii) the data is cone beam data, and (iii) the subject is scanned in a helical fashion. Mathematically, the "exact" reconstruction takes the form of a convolution back-projection, wherein both the convolution and the back-projection are 3D in nature. From a practical point of view, the 3D convolution is reduced or approximated by weighing a set of one-dimensional (1D) convolutions. The kernel for this 1D convolution is the classical 2D reconstruction kernel, i.e. a ramp convolver. The 1D convolution is performed in the direction of the tangent to the helix at the position of the vertex of the cone beam data, i.e., the location of the source 20. The weight for the convolved data along each ray depends on the ray's position in the cone as well as the position of the vertex of the cone relative to the reconstruction point.

In defining the terms and notation for the following rigorous mathematical derivation of the aforementioned exact inversion formula:

the subject to be reconstructed is represented by a function f from $R^3$ to R, and is of finite extent, i.e., of compact support; the unit sphere in $R^3$ is denoted by S, i.e., $S=\{x \in R^3 \mid \|x\|=1\}$; the inner product of two points x and y in $R^3$ is denoted by $<x, y>$; and, the Fourier transform of a function h is denoted by $\hat{h}$. For the 3D real function f, its Fourier transform is given by:

$$\hat{f}(\xi) = \int_{R^3} f(x) e^{-2i\pi \langle x, \xi \rangle} dx; \tag{1}$$

and, expressing equation (1) in a spherical coordinate system, gives:

$$\hat{f}(\xi) = \int_0^\infty \int_S \rho^2 f(\rho\theta) e^{-2i\pi\rho\langle\xi,\theta\rangle} d\theta d\rho. \tag{2}$$

The data is in the form of line integrals of the scanned subject f. Mathematically expressed, a positive half-line originating from a point V and extending in a direction $\alpha$, $\alpha \in S$, is the set $\{V+r\alpha \mid r \in [0\infty)\}$ so that the integral of f along the half-line is expressed as:

$$g_V(\alpha) = \int_0^\infty f(V + r\alpha) dr. \tag{3}$$

From this point of view, the set $\{g_V(\alpha) \mid \alpha \in S\}$ represents the set of line integrals of f in a cone of vertex V. Due to the finite extent of the function f, there exits a cone defined by a subset C of S such that $g_V(\alpha)=0$ if $\alpha$ is outside of C, assuming that the vertex V is outside of the support of the function f.

The classical inversion formula to reconstruct a 2D subject from its line integrals is based on the projection theorem which states that the 2D Fourier transform of the function to be reconstructed along a direction e is equal to the 1D Fourier transform of the integrals of the function along lines perpendicular to the direction $\theta$. A 3D version of this theorem uses planar integrals. More precisely, the 3D Fourier transform of the function to be reconstructed along a direction $\theta$ is equal to the 1D Fourier transform of the integrals of the function along planes perpendicular to the direction $\theta$. The function is then reconstructed by taking the inverse Fourier transform when its Fourier transform along all directions $\theta \in S$ are estimated. While no such projection theorem exists for fan beam or cone beam geometries, the Fourier transform of the function f is related to the cone beam data by the following lemma.

Extending the definition of $g_V(\alpha)$ to $\alpha \in R^3$, as a 3D function, the Fourier transform of $g_V$ satisfies the following relations:

$$\hat{g}_V(\theta) = \int_0^\infty \rho \hat{f}(\rho\theta) e^{2i\pi\rho\langle V,\theta\rangle} d\rho; \tag{4}$$

and, $$\hat{g}_V(\theta) - \hat{g}_V(-\theta) = \int_{-\infty}^\infty \rho \hat{f}(\rho\theta) e^{2i\pi\rho\langle V,\theta\rangle} d\rho. \tag{5}$$

In a fashion similar to the projection theorem, the second relation, equation (5) of the above lemma, shows that the 3D Fourier transform of f along a given direction $\theta \in S$ is estimated from the cone beam data provided that the vertex V of the cone describes a curve with the property that the inner product $<V, \theta>$ varies from $-\infty$ to $\infty$. Based on the projection theorem, it is deduced from the above relation that $$\hat{g}_V(\theta) - \hat{g}_V(-\theta) = -\frac{1}{2i\pi} R'_\theta f(\langle V, \theta \rangle), \tag{6}$$

where $R_\theta f(\rho)$ represents the integrals of f along the plane perpendicular to the direction $\theta$, at a distance $\rho$ from the origin of the coordinate system. Owing to the fact that the subject f is of finite extent, $R_\theta f(\rho)=0$ if the plane does not cut the subject. Consequently, the 3D Fourier transform of f along a given direction $\theta \in S$ is estimated from the cone beam data provided that the vertex V of the cone describes a curve with the property that the plane going through the vertex V and perpendicular to the direction $\theta$ sweeps through the entire subject.

In the reconstruction of f, the above condition of the curve is satisfied for all directions $\theta$. A bounded planar curve, such as a circle does not satisfy the condition. A well chosen portion of a helix does satisfy the condition. However, the number of intersection points of the planes containing a ray extending between the vertex and a point of reconstruction with that portion of the helical path followed by the source 20 to complete one reconstruction does not remain constant.

To compute the Fourier transform of f along a direction $\theta$ from equation (5) of the above lemma, functions $F_\theta$ are defined by the following equation:

$$F_\theta(u) = \int_0^\infty \rho \hat{f}(\rho\theta) e^{2i\pi\rho u} d\rho. \tag{7}$$

From this definition, it follows that:

$$F_\theta(u) - F_{-\theta}(-u) = \int_{-\infty}^\infty \rho \hat{f}(\rho\theta) e^{-2i\pi\rho u} d\rho. \tag{8}$$

In view of the lemma and the discussions following it, it is concluded that:

$$\hat{g}_V(\theta) = F_\theta(<V, \theta>) \tag{9}$$

and that if the function f is of compact support, then the function $(F_\theta - F_{-\theta})$ is also of compact support, i.e., the function is zero outside an interval $[-A, A]$. Consequently, $$\rho \hat{f}(\rho \theta) = \int_{-A}^{A} (F_\theta(u) - F_{-\theta}(-u)) e^{-2i\pi\rho u} d\rho. \quad (10)$$

Moreover, if the vertex V describes a parametric curve $\{\phi(\lambda)\}_{\lambda \in \Lambda}$, where $\Lambda$ is an interval of real numbers, such that there is a one-to-one correspondence between the interval $[-A, A]$, and the set $\{<\phi(\lambda), \theta>\}_{\lambda \in \Lambda}$, then by a substitution $u = <\phi(\lambda), \theta>$ in the above integral from equation (10), the following is obtained:

$$\rho \hat{f}(\rho \theta) = \quad (11)$$
$$\int_\Lambda (F_\theta(<\phi(\lambda), \theta>) - F_{-\theta}(<\phi(\lambda), -\theta>)) |<\phi'(\lambda), \theta>| e^{-2i\pi\rho<\phi(\lambda),\theta>} d\lambda.$$

A change of variables using cone beam data leads to:

$$\rho \hat{f}(\rho \theta) = \int_\Lambda (\hat{g}_{\phi(\lambda)}(\theta) - \hat{g}_{\phi(\lambda)}(-\theta)) |<\phi'(\lambda), \theta>| e^{-2i\pi\rho<\phi(\lambda),\theta>} d\lambda. \quad (12)$$

The estimation of f from cone beam data is done by estimating its Fourier transform along all directions e using the above equation (12). However, as pointed out earlier, if the curve described by the vertices of the cones is to be bounded, then the curve should be non-planar. A well chosen helical curve satisfies $u = <\phi(\lambda), \theta>$ for u in the interval $[-A, A]$. However, the solution is not unique, and the number of solutions depends on the value u, and the direction θ. For these reasons, the equation which relates the Fourier transform of f with cone beam data takes the multiplicity condition into account. That is:

$$\rho \hat{f}(\rho \theta) = \int_\Lambda (\hat{g}_{\phi(\lambda)}(\theta) - \hat{g}_{\phi(\lambda)}(-\theta)) |<\phi'(\lambda), \theta>| M(\theta, \lambda) e^{-2i\pi\rho<\phi(\lambda),\theta>} d\lambda, \quad (13)$$

where the "multiplicity function" M satisfies the condition $$M(\theta, s_0) + M(\theta, s_1) + \ldots + M(\theta, s_{\lambda\theta}) = 1 \quad (14),$$

when the $s_i$ 's are the roots of the equation $<\phi(s), \theta> = <\phi(\lambda), \theta>$, for $i = 0, 1, \ldots, \lambda\theta$. This multiplicity condition is expressed also by the following integral equation:

$$\int_\Lambda |<\phi'(s), \theta>| M(\theta, s) \delta(<\phi(\lambda) - \phi(s), \theta>) ds = 1. \quad (15)$$

In conclusion, the inversion formula to compute f from the cone beam data is obtained by writing the inverse Fourier transform using the spherical coordinate system:

$$f(x) = \int_\Lambda \int_0^\infty \rho \int_S (\hat{g}_{\phi(\lambda)}(\theta) - \quad (16)$$
$$\hat{g}_{\phi(\lambda)}(-\theta)) |<\phi'(\lambda), \theta>| M(\theta, \lambda) e^{2i\pi\rho<x-\phi(\lambda),\theta>} d\theta d\rho d\lambda.$$

In the above inversion formula, i.e., equation (16), integration with respect to ρ first achieves:

$$f(x) = -\frac{i}{4\pi} \int_\Lambda \int_S (\hat{g}_{\phi(\lambda)}(\theta) - \quad (17)$$
$$\hat{g}_{\phi(\lambda)}(-\theta)) |<\phi'(\lambda), \theta>| M(\theta, \lambda) \delta'(<x - \phi(\lambda), \theta>) d\theta d\lambda,$$

owing to the relation:

$$\int_0^\infty \rho e^{2i\pi\rho t} d\rho = \frac{1}{4i\pi} \delta'(t) + \frac{1}{4\pi^2 t^2}, \quad (18)$$

and the fact that the function f is real. Consequently, to reconstruct f at x, a point of reconstruction, it suffices to employ the sufficiency condition stated as: any plane going through the point of reconstruction x intersects the portion of the curve defining the helical path of the vertex at least once.

For example, in the case of helical scanning, to reconstruct f(x), it suffices to collect the data in a revolution around the point x. For this reason, in the following derivation, it shall be assumed that the interval $\Lambda$ defining the curve described by the vertices of the cone beam satisfy this sufficient condition.

Owing to the fact that the function g is homogeneous, i.e., $$g_{\phi(\lambda)}(\alpha) = \frac{1}{\|\alpha\|} g_V \phi(\lambda) \left( \frac{\alpha}{\|\alpha\|} \right), \quad (19)$$

it follows that its 3D Fourier transform satisfies:

$$\rho^2 \hat{g}_{\phi(\lambda)}(\rho\theta) = \hat{g}_{\phi(\lambda)}(\rho\theta) \quad (20).$$

Consequently, the first inversion formula is rewritten as:

$$f(x) = \int_\Lambda Q(x, \lambda) d\lambda, \quad (21)$$

where, $$Q(x, \lambda) = \int_0^\infty \int_S \rho^2 (\hat{g}_{\phi(\lambda)}(\rho\theta) - \quad (22)$$
$$\hat{g}_{\phi(\lambda)}(-\rho\theta)) |<\phi'(\lambda), \rho\theta>| M(\theta, \lambda) e^{2i\pi\rho<x-\phi(\lambda),\theta>} d\theta d\rho.$$

Observing that the expression Q is the 3D inverse Fourier transform of the product of 3 functions, it is concluded that is a 3D convolution, i.e., $$Q(x,\lambda) = ((g_{\phi(\lambda)} - g_{\phi(\lambda)}^-) * q_\lambda) * I_\lambda)(x - \phi(\lambda)) \quad (23),$$

where $q_\lambda$ and $I_\lambda$ are the 3D Fourier transform of the functions defined by $|<\phi'(\lambda), \ldots>|$, and M respectively, and where $g^-_{\phi(\lambda)}$ is defined by the equation:

$$g_{\phi(\lambda)}^-(\alpha) = g_{\phi(\lambda)}(-\alpha) \quad (24).$$

It should be pointed out here that the final integration to compute f(x) is the backprojection which is 3D since the point x and the vertices of the cone $\phi(\lambda)$ are points in 3D space.

It is advantageous to carry out the convolution in a local coordinate system. This is mainly due to the nature of the function defining the convolver $q_\lambda$. Indeed, by definition:

$$q_\lambda(\xi) = \int_{R^3} |<\phi'(\lambda), \alpha>| e^{-2i\pi<\xi,\alpha>} d\alpha. \quad (25)$$

Figure 2:
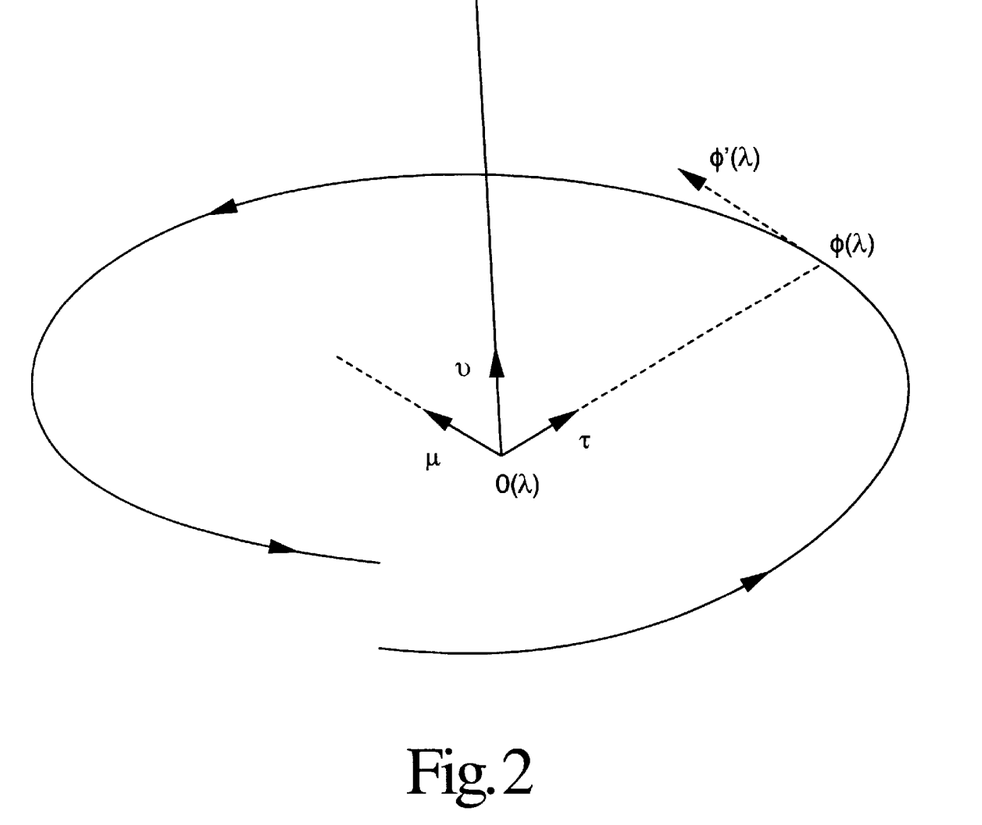

In a local coordinate system defined by the 3D unit vectors τ along $\phi(\lambda)$, $\mu$ along $\phi'(\lambda)$, and ν the third vector equal to the tensor product of $\tau$ and $\mu$ (see FIG. 2) the above expression becomes:

$$q_\lambda(t, u, v) = \|\phi'(\lambda)\| \int_{-\infty}^{\infty}\int_{-\infty}^{\infty}\int_{-\infty}^{\infty} |b| e^{-2i\pi(at+bu+cv)} da\, bd\, c. \quad (26)$$

Hence, $$q_\lambda(t, u, v) = -\frac{\|\phi'(\lambda)\|}{2\pi^2 u^2} \delta(t)\delta(v). \quad (27)$$

From the above expression of $q_\lambda$, it is concluded that if the computation is carried out in the local coordinate system, the 3D convolution $g_{\phi(\lambda)}*q_\lambda$ is reduced to a set of 1D convolutions. Below provides an explicit computation of $g_{\phi(\lambda)}*q_\lambda$ $(x-\phi(\lambda))$ in terms of line integral data.

By definition, $$g_{\phi(\lambda)} * q_\lambda(x - \phi(\lambda)) = \int_{R^3} g_{\phi(\lambda)}(x - \phi(\lambda) - \xi) q_\lambda(\xi) d\xi. \quad (28)$$

In the above local coordinate system, using the expression of $q_\lambda$, the following is obtained:

$$g_{\phi(\lambda)} * q_\lambda(x - \phi(\lambda)) = \quad (29)$$
$$-\frac{\|\phi'(\lambda)\|}{2\pi^2} \int_{R^3} g_{\phi(\lambda)}(x - \phi(\lambda) - (t, u, v))\delta(t)\delta(v)\frac{1}{u^2} dt\, dv\, du.$$

Hence, after integrating with respect to the variables t and v:

$$g_{\phi(\lambda)} * q_\lambda(x - \phi(\lambda)) = -\frac{\|\phi'(\lambda)\|}{2\pi^2} \int_{-\infty}^{\infty} g_{\phi(\lambda)}(P - \phi(\lambda))\frac{1}{u^2} du, \quad (30)$$

where $P=x-(0,u,0)$. To express the integral in terms of line integrals of f, the homogeneity property of $g_{\phi(\lambda)}$ is used, i.e., $$g_{\phi(\lambda)}(P - \phi(\lambda)) = \frac{1}{\|P - \phi(\lambda)\|} g_{\phi(\lambda)}\left(\frac{P - \phi(\lambda)}{\|P - \phi(\lambda)\|}\right). \quad (31)$$

Figure 3:
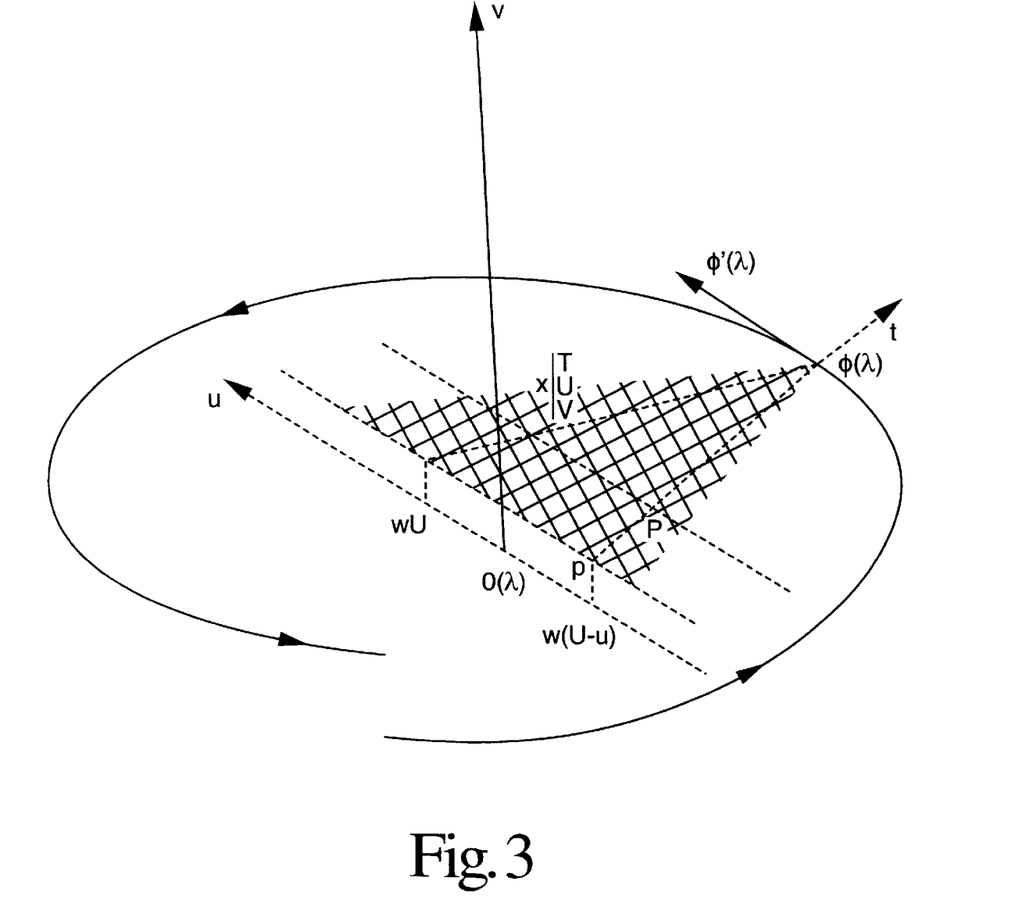

Defining p as the intersection of $\phi(\lambda)P$ with the plane $O(\lambda)$, u, v, (see FIG. 3), when $h_\lambda(P)$ represents the line integral of the function f along the line $\phi(\lambda)p$, the following equation is achieved:

$$g_{\phi(\lambda)}(P - \phi(\lambda)) = \frac{1}{\|P - \phi(\lambda)\|} h_\lambda(p). \quad (32)$$

Where (T,U,V) are the coordinates of the point x in the local coordinate system, and $R=\|O(\lambda)\phi(\lambda)\|$, the coordinates of the point p are $(0, w(U-u), wV)$ with:

$$w = \frac{R}{R-T}. \quad (33)$$

Furthermore, $$\frac{1}{\|P - \phi(\lambda)\|} = \frac{w}{\sqrt{R^2 + w^2(U-u)^2 + w^2 V^2}}. \quad (34)$$

Consequently, $$g_{\phi(\lambda)} * q_\lambda(x - \phi(\lambda)) = \quad (35)$$
$$-w\frac{\|\phi'(\lambda)\|}{2\pi^2} \int_{-\infty}^{\infty} \frac{h_\lambda(w(U-u), wV)}{\sqrt{R^2 + w^2(U-u)^2 + w^2 V^2}} \frac{1}{u^2} du.$$

In other words, $$g_{\phi(\lambda)} * q_\lambda(x - \phi(\lambda)) = -w^2 \int_{-\infty}^{\infty} H_\lambda(u, v) \frac{1}{(wU-u)^2} du, \quad (36)$$

where $H_\lambda$ is the weighted line integral data defined by:

$$H_\lambda(u, v) = \frac{\|\phi'(\lambda)\|}{2\pi^2 \sqrt{R^2 + u^2 + v^2}} h_\lambda(u, v). \quad (37)$$

The above calculation leads to the conclusion that $g_{\phi(\lambda)}*q_\lambda$ $(x-\phi(\lambda))$ is not 0 only if $x-\phi(\lambda)$ is in one half of the space separated by the plane going through $\phi(\lambda)$ and perpendicular to the t axis. This half space is denoted by $E^+$.

From a direct integral computation, it is shown that:

$$g_{\phi(\lambda)}^{-}*q_\lambda(\alpha) = g_{\phi(\lambda)}*q_\lambda(-\alpha) \quad (38).$$

Hence $g_{\phi(\lambda)}*q_\lambda(\alpha)$ is not 0 if $\alpha$ is in $E^-$, the complement of $E^+$. Note further that in the local coordinate system, the expression of $q_\lambda$ is the classical 2D reconstruction kernel or ramp function, and hence, is independent of the position of the vertex $\phi(\lambda)$. For this reason, $q_\lambda$ is from here on denoted by q to simplify notation.

Based on the definition of convolution, the following equation is achieved:

$$Q(x, \lambda) = \int_{R^3} ((g_{\phi(\lambda)} - g_{\phi(\lambda)}) * q)(y) I_\lambda(x - \phi(\lambda) - y) dy. \quad (39)$$

This integration is carried out in the local coordinate system with the origin at $\phi(\lambda)$. Denoting the half sphere centered at $\phi(\lambda)$ in the half-space $E^+$ by $S^+$, and the other half sphere by $S^-$, the following is derived:

$$Q(x, \lambda) = \int_0^\infty \rho^2 \int_{S^+} g_{\phi(\lambda)} * q(\rho a) I_\lambda(X - \phi(\lambda) - \rho a) da\, d\rho - \quad (40)$$
$$\int_0^\infty \rho^2 \int_{S^-} g_{\phi(\lambda)} * q(\rho a) I_\lambda(X - \phi(\lambda) - \rho a) da\, d\rho.$$

Since, $$g_{\phi(\lambda)} * q(\rho a) = \frac{1}{\rho^2} g_{\phi(\lambda)} * q(\rho a), \quad (41)$$

it follows that:

$$Q(x, \lambda) = \int_0^\infty \rho^2 \int_{S^+} g_{\phi(\lambda)} * q(a) I_\lambda(X - \phi(\lambda) - \rho a) da\, d\rho - \quad (42)$$
$$\int_0^\infty \rho^2 \int_{S^-} g_{\phi(\lambda)} * q(-a) I_\lambda(X - \phi(\lambda) - \rho a) da\, d\rho.$$

After making a change of variables in the second integral, and then interchanging the order of integration, it is concluded that:

$$Q(x, \lambda) = \int_{S^+} g_{\phi(\lambda)} * q(a) \int_{-\infty}^{\infty} I_\lambda(x - \phi(\lambda) - \rho a) d\rho da. \quad (43)$$

Figure 4:
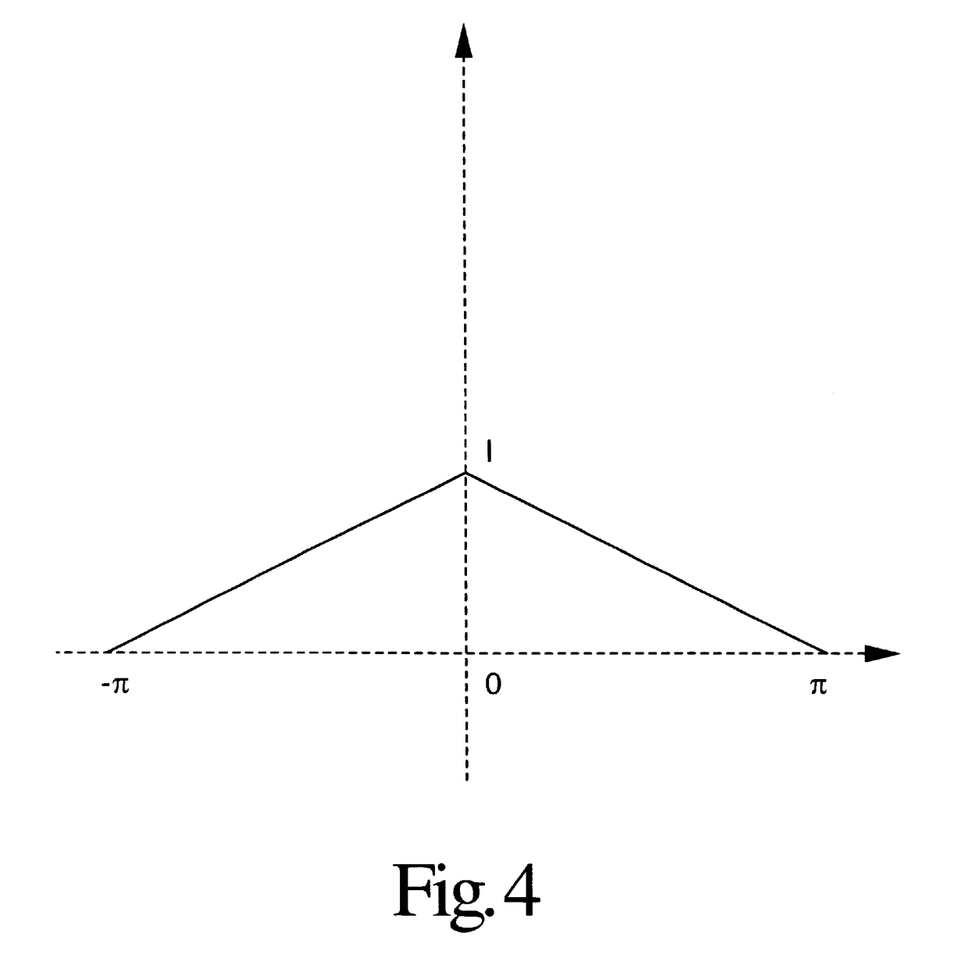

By definition, $I_\lambda$ is the 3D Fourier transform of the multiplicity function $M_\lambda$. Herein, a special form of $M_\lambda$ is considered which corresponds to a special case of a family of multiplicity functions. More precisely, $$M_\lambda(\theta) = \frac{C(\lambda)}{\sum_{i=1}^{N(\lambda, \theta)} |\langle \phi'(\lambda_i), \theta \rangle|^m C(\lambda_i)}, \quad (44)$$

where $\lambda_i$'s are the roots of the equation $\langle \phi(s), \theta \rangle = \langle \phi(\lambda), \theta \rangle$, for $i=1, \ldots, N(\lambda, \theta)$, and C is a continuous function, such as a triangular function which satisfies $C(-\pi)=C(\pi)=0$, and $C(0)=1$, for example, such as the one shown in FIG. 4. By definition:

$$\int_{-\infty}^{\infty} I_\lambda(x - \phi(\lambda) - \rho a) d\rho = \int_{-\infty}^{\infty} \int_{R^2} M_\lambda(\alpha) e^{-2i\pi \langle x - \phi(\lambda) - \rho a, \alpha \rangle} d\alpha d\rho. \quad (45)$$

In this particular case, since the function $M_\lambda$ is independent of the radius, and integration with respect to the variable $\rho$ is done first to obtain:

$$\int_{-\infty}^{\infty} I_\lambda(x - \phi(\lambda) - \rho a) d\rho = \int_{R^3} M_\lambda(\alpha) e^{-2i\pi \langle x - \phi(\lambda), \alpha \rangle} \delta(\langle a, \alpha \rangle) d\alpha. \quad (46)$$

Figure 5:
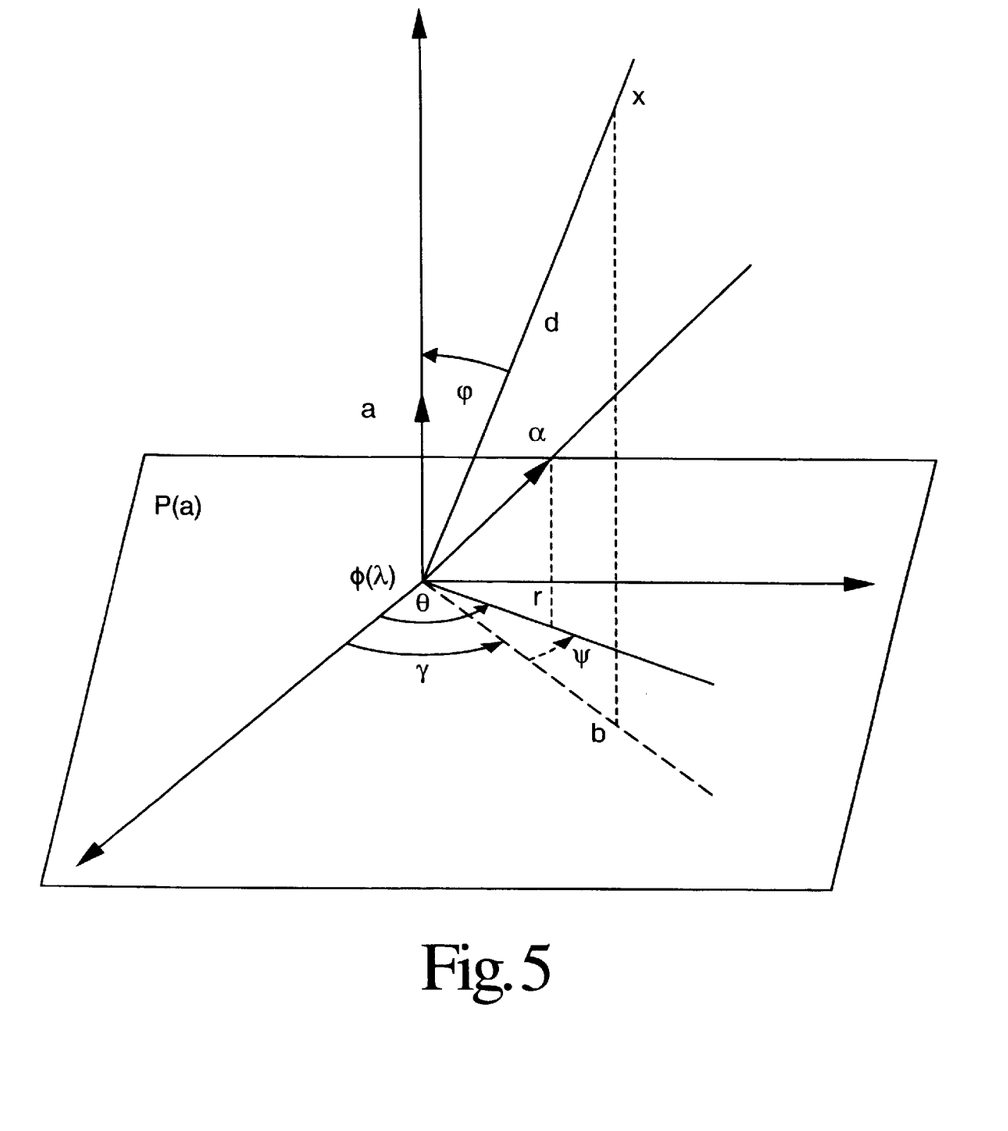

If we denote the plane going through $\phi(\lambda)$ and perpendicular to the vector a by P(a), the last integral from equating (46) is the 2D Fourier transform of the restriction of $M_\lambda$ on the plane P(a) evaluated at the orthogonal projection of $x-\phi(\lambda)$ onto P(a). Therefore, $$\int_{-\infty}^{\infty} I_\lambda(x - \phi(\lambda) - \rho a) d\rho = \quad (47)$$

$$\lim_{\epsilon \to 0} \int_{-\pi}^{\pi} \int_0^{\infty} r e^{-2\pi \epsilon r} M_{\lambda a}((r, \theta)) e^{-2i\pi rb\cos\psi} dr d\theta,$$

where b is the norm of the orthogonal projection of $x-\phi(\lambda)$ onto the plane P(a), and $\psi$ is the angle between the projections of $x-\phi(\lambda)$ and $\alpha$ onto P(a), as shown in FIG. 5.

This Fourier transform is a sum of a series with the first term equal to the Dirac distribution $\delta$ at $x-\phi(\lambda)$ weighted with a constant w(a). Note that, restricted to the plane P(a), the function $M_\lambda$ is a function $M_{\lambda a}$ of angle $\theta$ only (expressing a in polar coordinates in the plane P(a) as $(r, \theta)$), and is periodic with a period $2\pi$. If the projection of $x-\phi(\lambda)$ onto P(a) is $(b, \gamma)$ in this polar coordinate system (see FIG. 5), then:

$$\theta = \gamma + \psi \quad (48),$$

and hence, $$\int_{-\infty}^{\infty} I_\lambda(x - \phi(\lambda) - \rho a) d\rho = \quad (49)$$

$$\lim_{\epsilon \to 0} \int_{-\pi}^{\pi} \int_0^{\infty} r e^{-2\pi \epsilon r} M_{\lambda a}(\gamma + \psi) e^{-2i\pi rb\cos\psi} dr d\psi.$$

In this plane P(a), $$M_\lambda(\alpha) = M_{\lambda a}(\gamma + \psi) = \Sigma c_n(a, \lambda) e^{in(\gamma + \psi)} \quad (50).$$

Hence, $$\int_{-\infty}^{\infty} I_\lambda(x - \phi(\lambda) - \rho a) d\rho = \quad (51)$$

$$\lim_{\epsilon \to 0} \int_{-\pi}^{\pi} \int_0^{\infty} r e^{-2\pi \epsilon r} \sum c_n(z, \lambda) e^{in(\gamma + \psi)} e^{-2i\pi rb\cos\psi} dr d\psi.$$

After interchanging the order of summation and integrations, $$\int_{-\infty}^{\infty} I_\lambda(x - \phi(\lambda) - \rho a) d\rho = \lim_{\epsilon \to 0} \sum c_n(a, \lambda) J_n(b, \epsilon) e^{in\pi\gamma}, \quad (52)$$

where $$J_n(b, \epsilon) = \int_{-\pi}^{\pi} e^{in\psi} \int_0^{\infty} r e^{-2\pi r(\epsilon + ib\cos\psi)} dr d\psi. \quad (53)$$

The evaluation of the second integral of the above equation (53) leads to:

$$J_n(b, \epsilon) = \frac{1}{4\pi^2} \int_{-\pi}^{\pi} \frac{e^{in\psi}}{(\epsilon + ib\cos\psi)^2} d\psi. \quad (54)$$

These integrals are evaluated by contour integration around the unit circle using the residue theorem. More explicitly, putting $z = e^{i\psi}$ gives:

$$J_n(b, \epsilon) = \frac{1}{4\pi^2} \oint \frac{z^n dz}{iz\left(\epsilon + \frac{ib}{2}\left(z + \frac{1}{z}\right)\right)^2}. \quad (55)$$

In other words, $$J_n(b, \epsilon) = \frac{i}{\pi^2 b^2} \oint \frac{z^{n+1} dz}{(z - z_1)^2 (z - z_2)^2}, \quad (56)$$

where, $$z_1 = i\left(\frac{\epsilon}{b} + \sqrt{1 + \frac{\epsilon^2}{b^2}}\right), \quad (57)$$

and $$z_2 = i\left(\frac{\epsilon}{b} - \sqrt{1 + \frac{\epsilon^2}{b^2}}\right). \quad (58)$$

The above integral can be obtained by evaluating the residue of the integrand. Since $z_2$ is the only singular point inside the unit circle, it follows that this residue is the derivative of $z^{n+1}/(z-z_1)^2$ evaluated at $z_2$ multiplied by $2i\pi$. A straightforward calculation of this residue leads to:

$$J_n(b, \epsilon) = \frac{i^n b \left(\frac{\epsilon}{b} - \sqrt{1 + \frac{\epsilon^2}{b^2}}\right)^n \left(n\sqrt{1 + \frac{\epsilon^2}{b^2}} + \frac{\epsilon}{b}\right)}{2\pi\sqrt{b^2 + \epsilon^2}^3}. \qquad (59)$$

In particular, $$J_0(b, \epsilon) = \frac{\epsilon}{2\pi\sqrt{b^2 + \epsilon^2}^3}. \qquad (60)$$

It is observed that as $\epsilon \to 0$, $J_0(b, \lambda) \to \delta(b)/(2|b|)$ and $J_n(b, \lambda) \to n(-i)^n/(2\pi b^2)$ for $n>0$. Using the above results, the following is achieved:

$$Q_n(x,\lambda) = \Sigma Q_n(x,\lambda) e^{in\gamma} \qquad (61),$$

where $$Q_n(x, \lambda) = \lim_{\epsilon \to 0} \int_{S^+} g_{\phi(\lambda)} * q(a) c_n(a, \lambda) J_n(b, \epsilon) e^{in\gamma} da. \qquad (62)$$

A thorough computation of the convolution with the first term of the series is given below. The integration of this first term of this series is carried out in the polar coordinate system at $\phi(\lambda)$, where the third axis is going through the reconstruction point x. If p is the angle of an arbitrary vector a in $S^+$ with this third axis, and $d=\|x-\phi(\lambda)\|$ (see FIG. 4), then:

$$b = -d\sin\phi \qquad (63).$$

Hence, based on the above computations, $$Q_0(x, \lambda) = \frac{1}{2\pi} \lim_{\epsilon \to 0} \int_{S^+} g_{\phi(\lambda)} * q(a) c_0(a, \lambda) \frac{\epsilon}{(d^2 \sin^2\varphi + \epsilon^2)^{3/2}} da. \qquad (64)$$

In other words, $$Q_0(x, \lambda) = \qquad (65)$$

$$\frac{1}{2\pi} \lim_{\epsilon \to 0} \int_0^{2\pi} \int_{-\frac{\pi}{2}}^{\frac{\pi}{2}} |\sin\varphi| g_{\phi(\lambda)} * q(a) c_0(a, \lambda) \frac{\epsilon}{(d^2 \sin^2\varphi + \epsilon^2)^{3/2}} d\varphi d\theta.$$

Substituting sine by u, and $\epsilon/d$ by $\eta$, the following is derived:

$$Q_0(x, \lambda) = \qquad (66)$$

$$\frac{1}{2\pi d^2} \lim_{\epsilon \to 0} \int_0^{2\pi} \int_{-1}^{1} \frac{g_{\phi(\lambda)} * q(a) c_0(a, \lambda)}{\sqrt{1-u^2}} \frac{\eta}{u^2 + \eta^2} \frac{|u|}{\sqrt{u^2 + \eta^2}} du d\theta.$$

The evaluation of this limit gives:

$$Q_0(x, \lambda) = \frac{2\pi}{\|x - \phi(\lambda)\|} g_{\phi(\lambda)} * q(a_x) c_0(a_x, \lambda), \qquad (67)$$

where $a_x$ is the unit vector going through $\phi(\lambda)$ and the reconstruction point x. This relation shows that the first term of the series expressing Q is obtained by weighing the convolved data along the unit vector going through the reconstruction point. The weight is proportional to the summation of the multiplicity function values corresponding to all the planes going through $\phi(\lambda)$ and x, and is inversely proportional to the squared of the distance from $\phi(\lambda)$ to x.

Therefore, mathematically, the reconstruction of a three dimensional object defined by a function f is given by the following quadrature $$f(x) = \int_\Lambda Q(x, \lambda) d\lambda, \qquad (68)$$

where x is a point of reconstruction in 3D space, $Q(x, \lambda)$ is a three dimensional convolution of three functions evaluated at $(x-\phi(\lambda))$. This quadrature is a mathematical representation of a 3D backprojection. The inversion formula assumes that, for each, data corresponds to line integrals in a cone with vertex at $\phi(\lambda)$, and that the set of vertices $\{\phi(\lambda)|\lambda\in\Lambda\}$ is a differentiable curve in 3D space which satisfies the following property: any plane going through the point of reconstruction x intersects the curve at least once. The convolution $Q(x, \lambda)$ consists of three terms. The first term depends on line integrals of f or "collected data", the second term depends solely on the slope $\phi'(\lambda)$, and the last term depends on the number of intersection points of the curve $\{\phi(\lambda)|\lambda\in\Lambda\}$ with planes going through the reconstruction point x. Moreover, the convolution $Q(x, \lambda)$ is conveniently computed in a local coordinate system with one of the axis being parallel to the tangent vector $\phi'(\lambda)$. Being that the third term of the convolution is constant, or at least approximated by a (ray-dependent) multiplicative function, the 3D convolution $Q(x, \lambda)$ is obtained by performing a 1D convolution of "pre-weighted data" $H_\lambda$ along rays within the plane parallel to the tangent vector $\phi'(\lambda)$ and going through both the vertex $\phi(\lambda)$ and the reconstruction point x. The convolver is the classical ramp convolver which is used in 2D reconstruction.

Even though the derivation of the inversion formula assumes knowledge of line integral data in a cone, the computation of the convolution to compute f(x) uses only data within a plane or fan parallel to the tangent vector $\phi'(\lambda)$ and going through both the vertex $\phi(\lambda)$ and the reconstruction point x, for each position of the vertex $\phi(\lambda)$. For this reason, data may be truncated in the direction orthogonal to $\phi'(\lambda)$ The convolution of the Fourier transform of the multiplicity function with the data convolved with the classical ramp reconstruction filter is conveniently approximated by weighing the convolved data with a weight which depends on the vertex positions and ray positions within the vertex. For each ray position within a given vertex of the cone beam, the weight is precomputed and is proportional to the sum of all the multiplicity functions corresponding to all planes containing the ray. As well, for a given position of the vertex of the cone beam, the multiplicity function is a function of directions. For a given direction, the function depends on the number of intersections of the portion of the helix used in the backprojection with the plane going through the vertex and perpendicular to the direction. The multiplicity function is also defined to take into account on how much weight is given to the cone beam data. In a preferred embodiment, the weight is 1 if the position of the vertex is at the same level as the reconstruction point, and the weight goes to zero as the level of the position of the vertex of the cone goes a half-revolution away from the level of the reconstruction point.

In a preferred embodiment, the helical path followed by the vertex or source 20 relative to the subject is described by:

$$\phi(\lambda) = (R\cos\omega\lambda, R\sin\omega\lambda, \sigma\lambda) \qquad (69),$$

with constants ω and σ derived from the speeds of rotation of the source 20 and translation of the support 30. The tangent vector φ'(λ) is given by:

$$\phi'(\lambda)=(-R\omega\sin\omega\lambda,\ R\omega\cos\omega\lambda,\sigma). \tag{70}$$

Hence, $$\|\phi'(\lambda)\| = \sqrt{R^2\omega^2 + \sigma^2}\ . \tag{71}$$

For each view, the following 3 orthonormal vectors defining the local coordinate system are computed:

$$\tau=(\cos\omega\lambda,\sin\omega\lambda,0); \tag{72}$$

$$\mu = (-R\omega\sin\omega\lambda,\ R\omega\cos\omega\lambda,\ \sigma)\bigg/\sqrt{R^2\omega^2 + \sigma^2}\ ; \tag{73}$$

and, $$\nu = (\sigma\sin\omega\lambda,\ -\sigma\cos\omega\lambda,\ R\omega)\bigg/\sqrt{R^2\omega^2 + \sigma^2}\ . \tag{74}$$

In this local coordinate system, the coordinates (T, U, V) of the reconstruction point x are obtained by taking the inner products T=<X, τ>, U=<X, μ>, and V=<X, ν>, where X=x−(0,0, σλ). The ratio w=R/(T−R) is computed in order to find the ray going trough the reconstruction point x, and to provide the weight for the backprojection. The vertex of the cone is determined by the above computed value V. Earlier results show that the convolution backprojected from a particular view is the 1D convolution of the pre-weighted data along a fan going through the reconstruction point, the vertex of the cone, and parallel to the tangent vector of the helix. In this particular case, the convolved data is taken along 3 fans, each received by a corresponding front, center, and back ring of radiation detectors 40. The convolved data to be backprojected at this view is obtained by performing a 2D interpolation of the convolved data of the 3 fans based on the index of the ray deduced from wU, and the index of the cone vertex deduced from V (see FIG. 6). The quadrature of the inversion formula is approximated by a finite sum of these backprojected values, from a preselected first view to a preselected last view. For any given view, the convolved data along the 3 fans are done based on the results previously established herein. More precisely, line integrals which are proportional to the fan data are pre-weighted first to generate 3 fans of $H_\lambda$. Each detector fan is assumed to be collected in the direction of the tangent vector. These pre-weighted 3 fans are then convolved with the image reconstruction kernel. The fans are again weighted and then backprojected into the image memory 60. In this manner, the image reconstruction is carried out.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of image reconstruction from partial cone beam data comprising:

(a) collecting the partial cone beam data in two-dimensional arrays, said collected data corresponding to rays of radiation diverging in two dimensions from a common vertex as the vertex travels along a curve with each element of the data related to line integrals of an object being reconstructed taken along each ray;

(b) defining a local coordinate system;

(c) pre-weighting the data;

(d) computing a one-dimensional convolution of the pre-weighted data in the local coordinate system along a direction which is tangential to the curve along which the vertex travels;

(e) weighting the convolved data; and, (f) three-dimensionally backprojecting the weighted convolution.

2. The method according to claim 1, wherein for each position of the vertex as it travels along the curve, the data collected is not truncated in a direction parallel to the tangent of the curve at the position of the vertex and is truncated in at least one other orthogonal direction.

3. The method according to claim 2, wherein the curve along which the vertex travels is a differentiable curve in three-dimensional space arranged such that any plane going through a point of reconstruction intersects the curve at least once.

4. The method according to claim 3, wherein the curve defines a helical path.

5. The method according to claim 4, wherein a kernel for the one-dimensional convolution of the pre-weighted data is a ramp convolver.

6. The method according to claim 5, wherein the weighting of the convolved data is proportional to a summation of values of a multiplicity function, said values corresponding to all planes going through the vertex and the point of reconstruction.

7. The method according to claim 6, wherein values of the multiplicity function are determined based on a number of intersections corresponding planes going through the vertex and the point of reconstruction have with a portion of the helical path traveled by the vertex to collect enough data for one complete reconstruction.

8. The method according to claim 7, wherein the multiplicity function includes terms corresponding to each intersection, said terms having values based on the intersections' relative level to the point of reconstruction.

9. The method according to claim 8, wherein when intersections are at a level equal to that of the point of reconstruction their corresponding terms are fully valued, and as intersections gradually go to a level one half revolution away from that of the point of reconstruction their corresponding term values gradually go to zero.

10. The method according to claim 6, wherein the weighting of the convolved data is inversely proportional to the square of the distance between the vertex and the point of reconstruction.

11. The method according to claim 1, wherein image reconstruction takes place from full cone beam data and full cone beam data is collected in step (a).

12. A CT scanner comprising:

a first gantry which defines an examination region;

a rotating gantry mounted on the first gantry for rotation about the examination region;

a source of penetrating radiation arranged on the rotating gantry for rotation therewith, said source of penetrating radiation emitting a cone-shaped beam of radiation that passes through the examination region as the rotating gantry rotates;

a subject support which holds a subject being examined at least partially within the examination region, wherein at least one of the first gantry and the subject support is translated such that the subject passes through the examination region while the rotating gantry is rotated and the source of penetrating radiation follows a helical path relative to the subject;

a two-dimensional array of radiation detectors arranged to receive the radiation emitted from the source of penetrating radiation after it has traversed the examination region;

a reconstruction processor which reconstructs images of the subject from data collected by the two-dimensional array of radiation detectors, said reconstruction processor including;

- a first data processor which pre-weights the data;
- a convolver which takes the data from the first data processor and performs a one-dimensional convolution on it in a local coordinate system along a direction which is tangential to the helical path;
- a second data processor which takes the data from the convolver and weights it; and,
- a backprojector which takes the data from the second data processor and three-dimensionally backprojects it into an image memory; and, a human viewable display which accesses the image memory to display reconstructed images of the subject.

13. The CT scanner according to claim 12, wherein for each position of the penetrating radiation source along the helical path, the data collected is not truncated in a direction parallel to the tangent of the helical path at the position of the penetrating radiation source and is truncated in at least one other orthogonal direction.

14. The CT scanner according to claim 13, wherein the convolver employs a ramp function as a kernel for the one-dimensional convolution.

15. The CT scanner according to claim 14, wherein the second data processor multiplies the data by weights that are: (i) proportional to a summation of values of a multiplicity function, said values corresponding to all planes containing a ray extending from the position of the source of penetrating radiation to a point of reconstruction, and (ii) inversely proportional to the square of the distance between the position of the source of penetrating radiation and the point of reconstruction.

16. The CT scanner according to claim 15, wherein each value of the multiplicity function is determined based on a number of intersections its corresponding plane has with an amount of the helical path followed by the source of penetrating radiation, said amount allowing enough data collection for one complete reconstruction.

17. The CT scanner according to claim 16, wherein the multiplicity function includes terms corresponding to each intersection, said terms having values based on their corresponding intersections' level relative to the point of reconstruction.

18. The CT scanner according to claim 17, wherein when intersections are at a level equal to that of the point of reconstruction, their corresponding terms are fully valued, and as intersections gradually go to a level one half revolution away from that of the point of reconstruction, their corresponding term values gradually go to zero.

* * * * *